United States Patent [19]

Udding

[11] Patent Number: 4,666,631

[45] Date of Patent: May 19, 1987

[54] PROCESS FOR THE PREPARATION OF AN AZIDOSULPHONYLBENZOIC ACID

[75] Inventor: Anne C. Udding, Amsterdam, Netherlands

[73] Assignee: Shell Oil Company, Houston, Tex.

[21] Appl. No.: 819,953

[22] Filed: Jan. 21, 1986

[30] Foreign Application Priority Data

Aug. 16, 1985 [GB] United Kingdom ............... 8520583

[51] Int. Cl.$^4$ .......................................... C07C 117/00
[52] U.S. Cl. ................................................... 260/349
[58] Field of Search ........................................ 260/349

[56] References Cited

U.S. PATENT DOCUMENTS

| | | | |
|---|---|---|---|
| 2,485,116 | 10/1949 | Savard | 260/349 X |
| 2,625,565 | 1/1953 | Snell et al. | 260/349 X |
| 2,680,120 | 6/1954 | Gregory | 260/349 |
| 2,830,029 | 4/1958 | Adams | 260/349 UX |
| 2,865,932 | 12/1958 | MacMullen et al. | 260/349 |
| 3,347,870 | 10/1967 | Rutschmann et al. | 260/349 |
| 3,373,181 | 3/1968 | Linden et al. | 260/349 X |
| 3,376,127 | 4/1968 | McConnell et al. | 260/349 UX |
| 4,002,651 | 1/1977 | Marsden et al. | 260/349 |

OTHER PUBLICATIONS

Patai, (editor); "The Chemistry of the Azido Group", (1971), p. 175; Interscience Pub., N.Y.–London.

*Primary Examiner*—Joseph P. Brust
*Attorney, Agent, or Firm*—Peter A. Bielinski

[57] ABSTRACT

The invention relates to a process for the preparation of an azidosulphonylbenzoic acid which comprises reacting a water-soluble salt of a chlorosulphonylbenzoic acid with hydrazine ($N_2H_4$) in an aqueous medium, reacting the obtained hydrazinosulphonylbenzoic acid salt with nitrous acid in the same aqueous medium, acidifying the resulting aqueous solution comprising the azidosulphonylbenzoic acid salt, to precipitate the azidosulphonylbenzoic acid and separating the azidosulphonylbenzoic acid. The process is a one-pot process, which differs from a known process in that the intermediate, being the hydrazinosulphonylbenzoic acid salt, is not isolated.

9 Claims, No Drawings

PROCESS FOR THE PREPARATION OF AN AZIDOSULPHONYLBENZOIC ACID

The invention relates to a process for the preparation of an azidosulphonylbenzoic acid, to the azidosulphonylbenzoic acid so prepared and to its use as a carboxylation agent in elastomers.

BACKGROUND OF THE INVENTION

From "Houben-Weyl, Methoden der Organishcen Chemie, IX", page 653 it is known to prepare azidosulphonylbenzenes either by reacting chlorosulphonylbenzenes with sodiumazide or by reacting hydrazinosulphonylbenzenes with sodiumnitrite. It is further known from J. Chem. Soc. (C), 1968, pages 11-16, to prepare azidosulphonylbenzoic acids by reacting the chlorosulphonylbenzoic acids with hydrazine hydrate in ethanol or dioxan at a low temperature, e.g. 0° C. After cautions acidification and generally recrystallization the corresponding hydrazinosulphonyl benzoic acids are obtained as crystals, which decompose at their melting point. The hydrazinosulphonylbenzoic acids are converted into the corresponding azidosulphonylbenzoic acids. Disadvantages in the process for preparing azidosulphonylbenzoic acids are the use of an organic solvent, e.g. ethanol or dioxan, the isolation of the hydrazide intermediate with recrystallization, the two step process and molar excess of hydrazine. A disadvantage of the use of sodiumazide is the limited availability and the expensiveness of the sodiumazide.

SUMMARY OF THE INVENTION

It is the object of the present invention to have a much simpler process for the preparation of azidosulphonylbenzoic acids. The invention relates to a process for the preparation of an azidosulphonylbenzoic acid which comprises reacting a water-soluble salt of a chlorosulphonylbenzoic acid with hydrazine ($N_2H_4$) in an aqueous medium, reacting the obtained hydrazinosulphonylbenzoic acid salt with nitrous acid in the same aqueous medium, acidifying the resulting aqueous solution comprising the azidosulphonylbenzoic acid salt, to precipitate the azidosulphonylbenzoic acid and separating the azidosulphonylbenzoic acid. It has been found, that the process according to the invention is much more economical than the two-step process.

DETAILED DESCRIPTION OF THE INVENTION

The chlorosulphonylbenzoic acids which may be used as starting compounds in the process according to the invention have the general formula

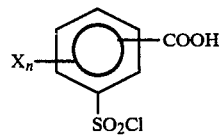

wherein the —COOH group is situated ortho, meta or para with respect to the —$SO_2Cl$ group, X is an alkyl-, alkoxy-, nitro-, carboxyl-, ester-, halogen- or hydroxy group and n is 0, 1, 2, 3 or 4. The starting compounds may thus be chlorosulphonylbenzoic acids, which contain only one —COOH group (in ortho, meta or para-position v.a.v the —$SO_2Cl$ group) or they may have been substituted at the other remaining positions by the above-mentioned groups. They may be substituted by a different group at a different position. The starting compounds are all considered to be derived from benzoic acid. The alkyl- or alkoxy group may preferably have from 1 to 20 carbon atoms and may be linear or branched. The ester group is preferably

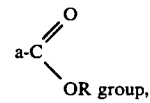

wherein R is a lower alkyl group of from 1 to 4 carbon atoms. The starting compounds can also comprise more than one —COOH group. The most preferred starting compound is 3-chlorosulphonylbenzoic acid. Preferred starting compounds are further the methyl-, methoxy-, hydroxy-, chloro- and bromo- derivatives of 3-chlorosulphonylbenzoic acid.

The water-soluble salt of the chlorosulphonylbenzoic acid is preferably an ammonium salt or an alkalimetal salt, more preferably the sodium or potassium salt. The water-soluble salt is obtained by dissolving the chlorosulphonylbenzoic acid in water in the presence of sodium- or potassium carbonate or sodium- or potassium bicarbonate or borate. Sodiumbicarbonate is preferred and may be present together with the other reaction component, namely the hydrazine, generally present in the form of hydrazine-hydrate. The chlorosulphonyl benzoic acid may be added in small portions or dropwise in the aqueous solution of hydrazine-hydrate and sodiumbicarbonate. The temperature during the reaction is generally low, e.g. below 25° C. The obtained hydrazinosulphonylbenzoic acid salt is then reacted with nitrous acid, which latter compound is generally prepared in situ by reacting sodiumnitrite with a strong acid, such as hydrogen chloride or sulfuric acid. The sodiumnitrite can be added in one portion to the obtained aqueous solution of hydrazinosulphonylbenzoic acid salt. In order to release the nitrous acid, the strong acid is added in small portions or dropwise to the aqueous solution. The reaction temperature is generally between 0° and 15° C. After acidification of the solution to pH 2 to 3, the resulting azidosulphonylbenzoic acid is precipitated. The compound is separated from the solution and if desired washed and dried, preferably at room temperature in vacuum.

The starting compound 3-chlorosulphonylbenzoic acid may be obtained by reacting 3 mol chlorosulfonic acid with 1 mol benzoylchloride according to the reaction equation

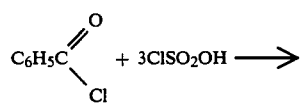

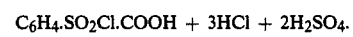

The azidosulphonylbenzoic acids, especially the 3-azidosulphonylbenzoic acid, are suitable as carboxylation agent for the preparation of carboxylated elastomers. An example of the latter is ethene-propene rubber, which easily reacts with the azidosulphonylbenzoic acid at a temperature of about 190° C. to 210° C.

EXAMPLE

In an Erlenmeyer glass are brought 1,5 liters of water, 1 mol hydrazine.hydrate (as an 80%w solution in water) and 2 mol NaHCO$_3$. To this mixture is added in small portions 1 mol 3-chlorosulphonylbenzoic acid under stirring at a temperature of 5° C. The resulting solution is stirred further for 2 h at a temperature of 5° C. The 1,1 mol NaNO$_2$ is added to the solution and subsequently in 2 h 2,1 mol HCl (HCl/H$_2$O, 1/1) is added to the solution. The temperature is maintained at 5° C., while holding the glass in an ice bath.

After acidifying the solution with HCl to a pH of about 2 to 3 the 3-azidosulphonylbenzoic acid precipitates. The precipitate is washed with water and dried at 20° C. in vacuum. There is obtained 0.85 mol 3-azidosulphonylbenzoic acid (melting point 122°–127° C. under decomposition), with infrared absorption 2160 cm$^{-1}$ and 1690 cm$^{-1}$. Yield is 85%.

What is claimed is:

1. A process for the preparation of azidosulphonylbenzoic acid which comprises reacting a water-soluble salt of chlorosulphonylbenzoic acid with hydrazine (N$_2$H$_4$) in an aqueous medium, reacting the obtained hydrazinosulphonylbenzoic acid salt with nitrous acid in the same aqueous medium and without isolation of the said hydrazinosulphonylbenzoic acid salt intermediate, acidifying the resulting aqueous solution comprising the azidosulphonylbenzoic acid salt, to precipitate the azidosulphonylbenzoic acid and separating the azidosulphonylbenzoic acid wherein said chlorosulphonyl-benzoic acid has the general formula

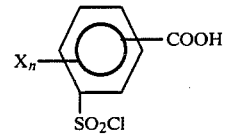

wherein X is selected from the group consisting of alkyl and alkoxy groups having from 1 to 20 carbon atoms, nitro groups, carboxyl groups, ester groups of the formula

where R is an alkyl group containing 1 to 4 carbon atoms, halogen groups and hydroxy groups and n is 0, 1, 2, 3 or 4, and
wherein the temperature during the reaction is below 25° C.

2. A process as claimed in claim 1 wherein the acid is 3-chlorosulphonylbenzoic acid.

3. A process as claimed in claim 1 wherein the water-soluble salt of the chlorosulphonylbenzoic acid is an alkali metal salt or ammonium salt.

4. A process as claimed in claim 3 wherein the alkali metal salt is the sodium or potassium salt.

5. A process as claimed in claim 1 wherein the water-soluble salt of the chlorosulphonylbenzoic acid is obtained by dissolving the chlorosulphonylbenzoic acid in water in the presence of sodium- or potassium carbonate or -bicarbonate.

6. A process as claimed in claim 1 wherein the nitrous acid is prepared in situ by reacting sodium nitrite with a strong acid.

7. A process as claimed in claim 7 wherein the strong acid is hydrogenchloride or sulphuric acid.

8. A process as claimed in claim 6 wherein the strong acid is added dropwise to the reaction solution, while releasing the nitrous acid slowly in the reaction solution.

9. A process as claimed in claim 8 wherein the reaction temperature is between 0° and 15° C.

* * * * *